United States Patent
Pappin et al.

(10) Patent No.: US 9,719,078 B1
(45) Date of Patent: Aug. 1, 2017

(54) PROTEASES FOR THE PRODUCTION OF N-TERMINAL ARGININYL- AND LYSINYL-PEPTIDES AND METHODS OF USE IN PROTEIN ANALYSIS

(71) Applicants: Darryl J. Pappin, Boxborough, MA (US); John P. Wilson, Huntington, NY (US); Jonathan J. Ipsaro, Cold Spring Harbor, NY (US)

(72) Inventors: Darryl J. Pappin, Boxborough, MA (US); John P. Wilson, Huntington, NY (US); Jonathan J. Ipsaro, Cold Spring Harbor, NY (US)

( * ) Notice: Subject to any disclaimer, the term of this patent is extended or adjusted under 35 U.S.C. 154(b) by 0 days.

(21) Appl. No.: 14/740,231

(22) Filed: Jun. 15, 2015

Related U.S. Application Data

(60) Provisional application No. 62/012,411, filed on Jun. 15, 2014.

(51) Int. Cl.
  *C12N 9/58* (2006.01)
  *G01N 30/72* (2006.01)
  *C12Q 1/37* (2006.01)
  *G01N 33/68* (2006.01)

(52) U.S. Cl.
  CPC ............. *C12N 9/58* (2013.01); *C12Q 1/37* (2013.01); *G01N 30/7233* (2013.01); *G01N 33/6848* (2013.01); *C12Y 304/24* (2013.01)

(58) Field of Classification Search
  None
  See application file for complete search history.

(56) References Cited

FOREIGN PATENT DOCUMENTS

WO   WO 2015/109405   *   7/2015

OTHER PUBLICATIONS

Nonaka, Takashi et al., "Characterization of a Thermostable Lysine-Specific Metalloendopeptidase from the Fruiting Bodies of Basidiomycete, Grifola frondosa", *J. Biochem.*, 1995, 118, 1014-1020.

Nonaka, Takashi et al., "Kinetic Characterization of Lysine-Specific Metalloendopeptidases from Grifola frondosa and Pleurotus ostreatus Fruiting Bodies", *J. Biochem.*, 1998, 124, 157-162.

Hori, Tetsuya et al., "Structure of a new 'aspzincin' metalloendopeptidase from Grifola frondosa: implications for the catalytic mechanism and substrate specificity based on several different crystal forms", *Acta Cryst.*, 2001, D57, 361-368.

Tatsumi, Hiroki, "232. Peptidyl-Lys metalloendopeptidase", Handbook of Proteolytic Enzymes 2$^{nd}$ Edn., 2004 *Elsevier Ltd.* 788-791.

Taouatas, Nadia et al., "Straightforward ladder sequencing of peptides using Lys-N metalloendopeptidase", *Nature Methods*, 2008, 5(5), 405-407.

Gauci, Sharon et al., "Lys-N and Trypsin Cover Complementary Parts of the Phosphoproteome in a Refined SCX-Based Approach", *Anal. Chem.* 2009, 81, 4493-4501.

Boersema, Paul, J. et al., "Straightforward and de Novo Peptide Sequencing by MALDI-MS/MS Using a Lys-N Metalloendopeptidase", *Molecular & Cellular Proteomics*, 2009, 8.4, 650-660.

Taouatas, Nadia et al., "Strong Cation Exchange-based Fractionation of Lys-N-generated Peptides Facilitates the Targeted Analysis of Post-translational Modifications", *Molecular & Cellular Proteomics*, 2009, 8.?, 190-200.

Taouatas, Nadia et al., "Evaluation of Metalloendopetidase Lys-N Protease Performance under Different Sample Handling Conditions", *Journal of Proteome Research*, 2010, 9(8), 4282-4288.

Wilson, John et al., "A thermostable N-terminal arginine and lysine specific protease for 1 hr digestion, simplified peptide fragmentation and increased MS/MS sensitivity", Poster presentation WP170, ASMS, Wednesday, Jun. 18, 2014.

Huesgen, Pitter, F. et al., "LysargiNase mirrors trypsin for protein C-terminal and methylation-site identification", *Nature Methods*, 2015, 12(1), 55-57.

* cited by examiner

*Primary Examiner* — Suzanne M Noakes
(74) *Attorney, Agent, or Firm* — Brian D. Gildea

(57) ABSTRACT

The invention relates to protease enzymes (that can be thermostable in some embodiments) with unique cleavage specificity as well as their production, isolation, activation and applications. These enzymes can be engineered for quick production and purification. The peptides produced by the action of these protease enzymes have unique properties for biochemical determination of protein sequence. In particular, using the steps of protease digestion, ionization of the specifically produced peptides and fragmentation of these peptides in a mass spectrometer, the amino acid sequence of the peptide may be read as a ladder from the N-terminus.

7 Claims, 4 Drawing Sheets

Protease cleavage specificity nomenclature.

Specificity of Ch therm and Co mil; trypsin included for comparison

Percent ion current in b- and y-ion series of Ch therm and Co mil; trypsin included for comparison. Note the exact inversion versus trypsin.

US 9,719,078 B1

PROTEASES FOR THE PRODUCTION OF N-TERMINAL ARGININYL- AND LYSINYL-PEPTIDES AND METHODS OF USE IN PROTEIN ANALYSIS

CROSS REFERENT TO RELATED APPLICATIONS

This application claims the benefit of U.S. Provisional Patent Application Ser. No. 62/012,411, filed on Jun. 15, 2014; herein incorporated by reference for any and all purposes.

The section headings used herein are for organizational purposes only and should not be construed as limiting the subject matter described in any way.

STATEMENT REGARDING FEDERALLY SPONSORED RESEARCH OR DEVELOPMENT

Not Applicable.

REFERENCE TO A SEQUENCE LISTING

Submitted on Aug. 23, 2015 was a copy of the Sequence Listing as a 'computer readable' (.txt) text file, named: "DJP001-US_SeqListingST25_txt"; which file was created on: Aug. 2, 2015; which file is 13 KB in size, and which file is incorporated herein by reference. This Sequence Listing was also submitted on Aug. 23, 2015 in PDF form into the image file for this application.

BRIEF DESCRIPTION OF DRAWINGS

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teaching in any way.

Figure 1:
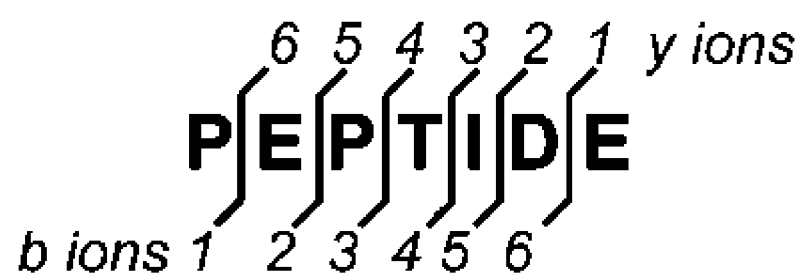
FIG. 1 illustrates peptide fragmentation and its associated nomenclature. When a peptide breaks into two pieces as a consequence of collision induced dissociation "CID" (for example, between P and T as show in FIG. 1) and the charge is kept on the N-terminal side of the peptide (to the left), the ion is called a "b-ion." In that particular case, the ion would be called a "b3-ion" and we would observe the fragment PEP. Likewise, when a charge is kept on the piece toward the C-terminal side, this is called a "y-ion." For a break between P and T as shown in FIG. 1, this would be a "y4 ion" and we would observe the fragment TIDE. Note that the direction of observable fragmentation is the same for other fragmentation techniques (e.g. electron capture dissociation "ETD") although the nomenclature is different.

All literature and similar materials cited in this application, including but not limited to patents, patent applications, articles, books and treatises, regardless of the format of such literature or similar material, are expressly incorporated by reference herein in their entirety for any and all purposes.

DESCRIPTION

All literature and similar materials cited in this application, including but not limited to patents, patent applications, articles, books and treatises, regardless of the format of such literature or similar material, are expressly incorporated by reference herein in their entirety for any and all purposes.

1. Field

The invention relates to the efficient, rapid and specific production of peptides with an N-terminal arginine or lysine for biochemical applications and analysis, as well as the determination of the sequence of these peptides using mass spectrometry. In some embodiments, the invention comprises multiple peptidase enzymes (including thermostable enzymes) engineered for high activity, easy expression and isolation, which cleave proteins specifically to the N-terminal side of lysine and arginine (or derivatives/analogs of said amino acids) to generate desirable peptides. In some embodiments, the invention relates to a method for purification, isolation and activation of these proteases and method and kit for using the proteases to specifically direct fragmentation in mass spectrometric analysis of peptides, thus determining peptide/protein sequence. Finally, the invention employs a device containing these proteases to prepare the desired peptides.

2. Introduction

Proteins form the structure and miniature natural machines (enzymes) that make life possible. Ultimately, it is at the level of proteins that health and disease distinguish themselves. Thus, efficient means to identify proteins and their differences are desirable to make advances in our understanding of human health and diagnose disease.

The study of all the proteins of an organism or tissue is termed "proteomics" and the "proteome" is the entire set of expressed proteins. While the tools for genomics are now highly developed and robust, proteomics has lagged significantly behind. One of the main causes of this disparity is that in genomics, material can be copied, or amplified, through polymerase chain reactions (PCR). Thus, even extremely small quantities of DNA or RNA can be brought to a level sufficient for more or less error-free reading, performed with many detectors in parallel.

In proteomics, no such amplification is possible. Detectors have thus become extremely sensitive but at some level, interference from background levels of other molecules, even those emanating from paint and the materials of buildings, make detection impossible. In addition, the complexity of the proteome is greater: one gene can become many proteins due to mechanisms such as alternative splicing and the activity of proteins themselves are regulated with many "switches" or post-translational modifications (PTMs), as well as proteolytic events. Furthermore, while all tissues of an organism have more or less the same genome, each tissue expresses different proteins, namely those which make it that specific tissue. Thus, the proteome is far more difficult to analyze than the genome.

While multiple techniques have been developed for protein analysis, mass spectrometry (MS) has become the tool of choice due to its speed and broad applicability. Mass spectrometers only work with charged molecules, or ions, and fortunately proteins have many charged centers. While whole proteins can be analyzed, the information garnered from such analyses becomes exponentially more complicated as a function of size. This approach, termed "top-down," is thus typically limited to the analysis of known sequences. The physics of the instrument also impose performance limitations, especially as the size of analyte molecule increases.

To circumvent these problems, a so-called "bottom-up" approach is commonly employed in which treatment with proteases cleaves proteins into smaller, more manageable fragments prior to MS analysis. This is the first step of the vast majority of MS protein analysis. In addition to favorable instrument performance, analysis of smaller molecules also speeds downstream data processing. The proteolytic step can be performed in solution on a mixture of proteins or an isolated protein. Alternatively, proteolysis can be performed on proteins separated in gels; comparative analysis of gels can be a useful way to identify changes between conditions or states such as health and disease.

Because the proteome is already complicated, proteases with known specificities are highly valued. With high specificity, a limited number of known peptides result from any given protein. With low or no specificity, the possible number of peptides for any given protein expands rapidly. The most commonly used protease is trypsin, a serine endoprotease widely expressed in the digestive system which cleaves C-terminally to arginine and lysine. To generate overlapping peptides and thus more fully decipher the sequence of a protein, multiple proteases are often used, for example trypsin and GluC, elastase, LysC, LysN or chymotrypsin.

These digestions usually run overnight, causing significant delay in experimental sample preparation. Reducing digestion times would result in significant gains in the efficiency of experimental analysis. Reduction in time has been achieved with the thermophilic enzyme thermolysin (J. Am. Chem. Soc. 2001 Feb. 28; 123(8): 1774-5. High-temperature protein mass mapping using a thermophilic protease. (Bark S J, Muster N, Yates J R 3rd, Siuzdak G.). However, because the enzyme has broad specificity of hydrophobic amino acids, this approach has significant limitations and has not been broadly implemented. Digestions with standard proteolytic enzymes can be performed at a temperature usually between room temperature and 37° C. While increased temperatures would temporarily speed the reaction, higher temperatures denature the enzymes widely used. Digestion times thus cannot be decreased. Some proteins, such as the prion protein of Mad Cow disease or amyloid fibrils in Alzheimer's disease, are highly resistant to standard conditions of proteolysis. Analysis of these proteins would also benefit from the use of increased temperatures because they denature tertiary structure and expose the protein backbone to proteases.

The second step of MS protein analysis is the separation of the peptides in time before their introduction into the mass spectrometer, where they are termed "precursor ions." This is typically achieved through some form of liquid chromatography (LC), often using reverse phase (RP) and/or cation exchange resins contained in very small capillary columns, often with an inner diameter from 250-50 um. These two separation steps are often combined on-line in a format termed MuDPIT (Multidimensional Protein Identification Technology) to increase separation power.

The third step of MS protein analysis is the ionization of the peptides, which is performed through primarily using two techniques. In the case of electrospray ionization (ESI), the chromatographic separation is directly coupled to the instrument. The analyte molecules are exposed to a high potential (voltage) as they exit the separation column, resulting in a very fine, highly charged spray. The droplets of this spray rapidly lose solvent and become smaller until only ionized peptides exist in the gas phase; these are taken into the instrument for analysis. MALDI or matrix-assisted laser desorption ionization is a different technique by which peptides can be brought into the gas phase. In MALDI, peptides are co-crystallized within a matrix. The matrix is exposed to a short laser pulse, which sublimates the matrix, thus bringing the peptides into the gas phase, and simultaneously ionizes them.

In the fourth step, once thus ionized and in the gas phase, the mass spectrometer determines the intensity of analyte ions (which correlates to the number of ions) through its measurable range of mass to charge ratios (m/z). These scans are often termed "precursor scans" (or MS1s) and are done at constant intervals of time. Any particular m/z value represents a potential "precursor ion" which can be further interrogated. Because in ESI they are being separated in time, the composition of precursor ions is constantly changing.

The mass spectrometer continues with the fifth step of the analysis, fragmentation of precursor ions. This begins with prioritization of the order of interrogation. Typically precursor ions are prioritized by intensity, with the most intense being interrogated first, then the next most intense, etc. for some number of prespecified scans until another MS is performed. The precursor ion of interest is isolated then exposed to a variety of fragmentation techniques. In collision induced dissociation (CID) also called collisionally activated dissociation (CAD), precursor ions are accelerated by an electrical potential to great speed (high kinetic energy) and allowed to collide with neutral gas molecules (e.g. argon or nitrogen). The gas phase collisions impart more and more energy to peptide molecules that it eventually breaks apart into smaller fragments consisting mainly of the y- and b-ion type for tryptic peptides. CID is the most widely used fragmentation technique. Alternative fragmentation techniques such as electron transfer dissociation (ETD) and electron capture dissociation (ECD) can also be employed which produce different types of ions and which offer the benefit of being more gentle to peptide modifications such as phosphorylation. Regardless how precursors are fragmented, the m/z values of fragment ions are then measured and stored for later use in determining the peptide sequence and thus protein identity.

Peptide sequence can be obtained either via de novo techniques, which attempt to translate fragmentation peaks to a sequence, or via database matching, in which known sequences are fragmented in silico and the experimental and computed spectra are compared either via cross correlation or probability based matching techniques; various combination of these also exist. Regardless of the method, the output of these methods is a list of potential matches (interpretations) ranked as function of confidence. In the case of unsequenced proteins such as antibody variable regions or samples from unsequenced organisms, only de novo approaches are suitable.

Because mass spectrometers can only detect charged species, these fragments themselves must also carry charge so they can be detected. In peptides produced from proteases, positive charges typically reside at the N-terminus and basic amino acids while negative charges reside at the C-terminus and acidic amino acids. Usually, mass spectrometers detect positive ions and thus the location of basic centers including the basic amino acids, Arg and Lys, as well as the N terminus, can be of primary importance. In the case of trypsin, which cuts to the C terminal side of Arg and Lys, the resulting peptide typically has one positive charge on the N terminal side (the N terminal amino terminus) and one on the C terminal side (the Arg or Lys), for example K[cut] PEPTIDER[cut](rest of protein).

During fragmented within the mass spectrometer, the charge of the original peptide will remain with the basic center(s) in the resulting fragments. In the above case, one basic center is at the N terminus (the N terminal amino group) and the other is at the C terminus (the arginine or lysine). Fragments where the charge is maintained on the N-terminal piece are called "b-ions" and fragments in which the charge is maintained on the C-terminal piece are called "y-ions" (see FIG. 1 below). Thus, in tryptic peptides where exists a positive charge exists on both ends of the molecules, both b- and y-ions are observed simultaneously. This same principle applies to other ion series (e.g. c- and t-ions in ETD).

For example, with reference to FIG. 1, when a peptide breaks into two pieces in CID (for example, between P and T) and the charge is kept on the N-terminal side of the peptide (to the left), the ion is called a "b-ion." In that particular case, the ion would be called a "b3-ion" and we would observe the fragment PEP. Likewise, when a charge is kept on the piece toward the C-terminal side, this is called a "y-ion." For a break between P and T this would be a "y4 ion" and we would observe the fragment TIDE. Note that the direction of observable fragmentation is the same for other fragmentation techniques (e.g. ETD) although the nomenclature is different.

This phenomenon superimposes two registers (frames of fragmentation) on top of each other, increasing uncertainty because neither person nor machine knows if an observed ionized fragment represents a part of the peptide from the N- or the C-terminal side. It also decreases sensitivity: signals are in essence split in intensity, with a portion of the molecules being detected as b-ions and the remainder as y-ions. This is disadvantageous particularly at the limit of detection. If all fragments were known to come specifically from one end of the peptide (i.e. all b- or y-ions), detection would become both more certain and more sensitive.

The desired fragmentation in which all (or nearly all) ions are b-ions (representing fragments beginning with the original N-terminal of the peptide) can be achieved by moving all basic centers (i.e. Arg and Lys) to the N-terminal end. With both the amino terminus (the intrinsic basic group of peptides) and the basic amino acid at the first position of the peptide, all positive charges tend to reside at the N-terminal of the peptide. Thus, upon fragmentation, predominately b-ions are observed—they are the only ones bearing charge—and a ladder can be easily read off from one peak to the next, the distance between them yielding the sequence of the peptide.

One attempt at achieving this was made in US patent no. 2010/0311098, "Method for determining the amino acid sequence of peptides." However, the activity there was specific only to lysine, frequently leaving arginine and thus a basic center somewhere in the middle of peptide and thus resulting in the same overlapping register issue found with trypsin. Were arginine extremely uncommon in proteins, this might be acceptable. However, arginine is present at a frequency of 5.53% in the UniProtKB/Swiss-Prot database, only 0.32% less frequent than lysine at 5.85%. Consequently, while Lys-N can sometimes generate a ladder, it will only do so in the absence of arginine; Lys-N thus does not represent a general approach to unambiguously determining the sequence of a peptide. In addition, the digestion times for Lys-N are, as is typical, overnight (18 hrs) at room temperature to 37 C. Finally, Lys-N does not allow for digestion at elevated temperatures to access difficult-to-digest proteins.

There thus exists need for enzymes, methods, kits and devices which 1) have N-terminal specificity for both lysine and arginine, thus maintaining charge on the N-terminal side of peptide fragments to yield a ladder of predominately N-terminal ions for all peptides, including those with arginine; and 2) which allow rapid digestion, preferably by operating at elevated temperatures.

DEFINITIONS

For the purposes of interpreting of this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

As used herein, the term "primer" refers to an oligonucleotide, whether natural or synthetic, which is capable of acting as a point of initiation of synthesis when placed under conditions in which primer extension is initiated or possible. Synthesis of a primer extension product which is complementary to a nucleic acid strand can be initiated in the presence of nucleoside triphosphates and a polymerase in an appropriate buffer at a suitable temperature. The term "primer" may refer to more than one primer, particularly in the case where there is some ambiguity in the information regarding one or both ends of the target region to be synthesized. For instance, if a nucleic acid sequence is inferred from a protein sequence, a "primer" generated to synthesize nucleic acid encoding said protein sequence can be a collection of oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence as set forth in SEQ ID NOs: 1-4 and can be designed based upon the degeneracy of the genetic code.

As used herein, the term "restriction endonucleases" and "restriction enzymes" refers to bacterial enzymes which cut double stranded DNA at or near a specific nucleotide sequence.

As used herein the term "gene" refers to the segment of DNA involved in producing a polypeptide chain; it includes regions preceding and following the coding region (leader and trailer) as well as intervening sequences (introns) between individual coding segments (exons).

As used herein, a coding sequence is "operably linked" to another coding sequence when RNA polymerase will transcribe the two coding sequences into a single mRNA, which can then be translated into a single polypeptide having amino acids derived from both coding sequences. The coding sequences need not be contiguous to one another so long as the expressed sequences ultimately process to produce the desired protein or polypeptide.

As used herein, the term "recombinant enzyme" refers to an enzyme produced by recombinant DNA techniques; i.e., produced from cells transformed by an exogenous DNA construct encoding the desired enzyme (e.g. the thermostable peptidase enzymes described herein).

As used herein, the term "synthetic enzymes" refers to those enzymes produced by chemical synthesis. Somewhat between recombinant and synthetic production techniques is production by in vitro translation or IVT. In this system, isolated protein synthesis machinery expresses the protein of interest upon addition of DNA engineered for ribosomal binding.

As used herein, the term "expression system" refers to any system capable of making or synthesizing protein, which may be through recombinant, IVT or chemical synthesis means.

As used herein, the terms "polypeptide" or "protein" are interchangeable and refer to a polymer in which the monomer subunits are amino acid residues which are joined together through amide bonds. When the amino acids are alpha amino acids, either the L-optical isomer or the D-optical isomer can be used, the L-isomers being preferred. The term "polypeptide" as used herein is intended to encompass any amino acid sequence and may optionally include modified sequences such as glycoproteins. The term "polypeptide" is specifically intended to cover naturally occurring proteins (and fragments thereof), as well as those which are recombinantly or synthetically generated, which occur in at least two different conformations wherein both conformations have the same or substantially the same amino acid sequence but have different three-dimensional structures. "Polypeptide" specifically covers proteins found in natural sources and those made by synthetic or recombinant processes regardless of their three dimensional conformation or structure.

As used herein, "fragments" refers to a portion of a naturally occurring protein or polypeptide. Fragments can have the same or substantially the same amino acid sequence as the naturally occurring protein fragment. A protein fragment can be produced through treatment with a protease.

As used herein, "substantially the same" means that an amino acid sequence is largely, but not entirely, the same, but retains a functional activity of the sequence to which it is related. In general two amino acid sequences are "substantially the same" (also sometimes referred to as "substantially homologous") if they are at least 85% identical (i.e. 85% homology in amino acid sequence). In some embodiments, they are substantially homologous if they are at least 90 percent Identical. In some embodiments, they are substantially homologous if they are at least 95 percent identical. In some embodiments, "substantially the same" refers to the situation where there is only one or two amino acid insertions, one or two amino acid deletions and/or one or two amino acid substitutions (i.e. a conservative variation) as compared with the SEQ ID NO referred to herein. When "substantially the same" is used, it also refers to comparing amino acid sequences of the same length or within one or two amino acid differences (longer or shorter) in total length.

The term "conservative variation" or "conservative variation" refers to the substitution of an amino acid residue for another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immuno-react with the unsubstituted polypeptide.

As used herein, a "coding sequence" or a "nucleotide sequence encoding" a particular enzyme refers to a nucleic acid sequence that can be transcribed and translated into an enzyme when placed under the control of appropriate regulatory sequences.

As used herein, "lysine" means L-lysine and derivatives thereof. For example, mono-, di- or tri-methyl lysine.

As used herein, "arginine" means L-arginine and derivatives thereof. For example, mono- or di-methyl arginine.

As used herein the term "isolated" means altered "by the hand of man" from its natural state; i.e., if it occurs in nature, it has been changed or removed from its original environment, or both. In some embodiments, "isolated" will refer to the product of a crude purification whereby only some of the components of the components of the environment in which it is produced are removed (for example, cellular debris removed from a cell lysate). In some embodiments, "isolated" will refer to the product of a substantial purification process such that the "isolated" material is substantially pure.

As used herein, "solid support" refers to any solid phase material. Solid support encompasses terms such as "resin", "bead', "film", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

As used herein, the term "thermostable peptidase" or "thermostable protease" refers to a protease capable of operating at temperatures significantly elevated from room or body temperature. For example, "thermostable" proteases described can be stable to heat and capable of performing its enzyme function at a temperature 50° C. before irreversible thermal denaturation degrades the enzymatic activity.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989).

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., Meth. Enzymol., 68, 90-99, (1979); the phosphodiester method of Brown et al., Method. Enzymol. 68, 109-151, (1979); the diethylphosphoramidite method of Beaucage et al., Tetrahedron Lett., 22, 1859-1862, (1981); the triester method of Matteucci et al., J. Am. Chem. Soc., 103, 3185-3191, (1981); or automated synthesis methods; and the solid support method of U.S. Pat. No. 4,458,066.

As used herein the term "plasmids" generally is designated herein by a lower case p preceded and/or followed by capital letters and/or numbers, in accordance with standard naming conventions that are familiar to those of skill in the art.

"Polynucleotide" or "nucleic acid sequence" refers to a polymeric form of nucleotides at least 10 bases in length. By "isolated nucleic acid sequence" is meant a polynucleotide that is not immediately contiguous with both of the coding sequence with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote; or which exists as a separate molecule (e.g., an eDNA) independent of other sequences. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA Thus, for instance, polynucleotides as used herein refers to, among others, single- and double-stranded DNA, DNA that is a mixture of single- and double-stranded regions, single- and double-stranded RNA, and RNA that is mixture of single and double-stranded regions, hybrid molecules comprising DNA and RNA that may be single-stranded or, more typically, double-stranded or a mixture of single- and double-stranded regions.

In addition, polynucleotide as used herein refers to triple stranded regions comprising RNA or DNA or both RNA and DNA The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, etc.

SUMMARY OF THE INVENTION

It should be understood that the order of steps or order for performing certain actions is immaterial so long as the present teachings remain operable or unless otherwise specified. Moreover, in some embodiments, two or more steps or actions can be conducted simultaneously so long as the present teachings remain operable or unless otherwise specified.

In some embodiments, this invention provides compositions and methods useful to determine the sequence of peptides, which thus enables the identification proteins and collections of proteins. Novel metalloproteases (including thermophilic varieties) specific for cleavage N-terminally to both lysine and arginine (below these metalloproteases are referred to herein as "ArgLysN"). The thermophilic varieties of these proteases are active at elevated temperatures at or exceeding 50° C. Such conditions can denature the tertiary structure of most mesophilic proteins, providing the advantages of decreased incubation time and proteolytic accessibility to difficult to digest proteins. This advantage is not possible with the proteases currently in wide use for MS analysis. Accordingly, protease enzyme embodiments of the present invention provide distinct advantages over previous enzymes used in MS protein analysis.

These novel protease enzymes disclosed herein usually require, for their catalytic activity, divalent cations of the group $Ca^{2+}$, $Cd^{2+}$, $Co^{2+}$, $Fe^{2+}$, $Ni^{2+}$, $Pb^{2+}$, $Rh^{2+}$, and $Zn^{2+}$ alone or in combination. In some embodiments, the presented proteases require the specific combination of both $Ca^{2+}$ and $Zn^{2+}$ for efficient activity. The protease enzymes of this invention can be monomeric as determined by ESI intact molecular weight measurement. In some embodiments, the polypeptide protease enzymes of the invention have a sequence as set forth in SEQ ID NOs: 1-4.

In some embodiments, the protease enzymes disclosed herein were engineered for greater activity by removal of N terminal prodomains and/or C-terminal domains. In some embodiments, efficient production and rapid isolation of the engineered protease was possible through fusion to heterologous amino acid septamer as given in SEQ ID NO: 5. In some embodiments, efficient production and rapid isolation of the engineered protease was possible through fusion to additional heterologous amino acid 17-mer as specified in SEQ ID NO: 6. Fusion with either SEQ ID NO: 5 or 6 also allows immediate removal of the protease from the digestion through exposure to IMAC resin, thus providing a convenient way to stop the proteolytic digestion.

The present invention addresses the problem of overlapping N- and C-terminal fragments by disclosing (polypeptide) protease enzymes with N-terminal Arg/Lys specificity, in contrast to Lys only. Thus, in some embodiments, the invention provides a method of determining a highly interpretable, unambiguous spectrum which can be interpreted without reference to databases. In MS analysis, embodiments of the invention further may comprise the steps of cleaving proteins into peptides with an N-terminally arginine or lysine in solution or in gels, at or above 50° C. for more rapid digestion, ionizing these peptides to generate precursor ions, breaking these precursor ions into fragments within the mass spectrometer through fragmentation techniques of CID, ETD or PSD and the predominant maintenance of charge by the fragments on the N-terminal side (b-ions in CID or PSD or c-ions in ETD), thus producing a simplified fragmentation ladder which can be unambiguously read by man or machine in de novo sequence interpretation or database searches. Additionally, by directing ion current in MS/MS spectra to specific fragments, sensitivity is increased. Thus, embodiments of this invention also relate to the combination of a thermostable ArgLysN metalloprotease polypeptide with the fragmentation techniques of CID, ETD or PSD and interpretation of the resulting sequence ladder.

In some embodiments, the invention may also relate to composition (e.g. a device) in which the thermostable ArgLysN is covalently coupled to a solid support, such as beads of sepharose (e.g. Example 3), magnetic or glass beads. Methods for immobilizing proteins to solid supports are fairly well known to those of ordinary skill in the art.

DESCRIPTION OF THE INVENTION

Proteases, a term synonymous with peptidases, are a kind of enzymes which cut the peptide backbone of proteins, thus typically producing smaller protein pieces. In the body they are essential to the digestion of food and are heavily involved in regulatory processes such as blood clotting and neural communication. Proteases comprise two classes: endoproteases, which cleave peptide bonds somewhere within the middle of a protein, and exoproteases, which remove amino acids from either the C or N terminal end of proteins. Proteases are alternatively subdivided by the mechanism of their action into serine, cysteine, aspartic acid, glutamic acid, threonine and metallo-proteases. A further class exists for those protease of unknown function.

Figure 2:
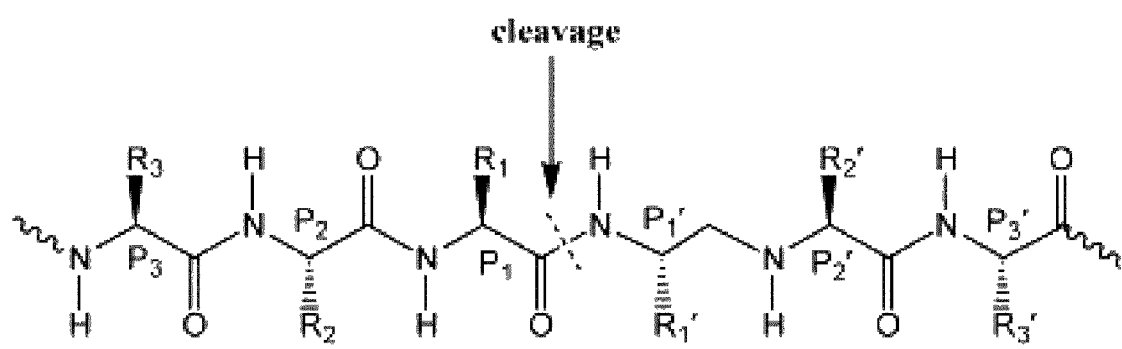
FIG. 2 illustrates protease cleavage specificity nomenclature.

In all cases, enzymes may be specific, cleaving next to one or a few amino acid residues (such as the case with trypsin) or a specific sequence of multiple amino acids (such as with thrombin), or nonspecific (such as the case with subtilisin), cleaving more or less randomly at any residue. Enzyme specificity is represented by the nomenclature of FIG. 2. Sites moving N-terminal are called $P_n$, where n is 1 for the amino acid directly N-terminal to the site of cleavage. Likewise sites moving C-terminal from the site of cleavage are called $P_n'$, where n is 1 for the amino acid directly C-terminal to the site of cleavage. In the case of trypsin, the specificity is P1={K,R} or the P1 site (which becomes the new free C-terminal end) must be lysine or arginine. In the case of thrombin, specificity is LVPR[cleavage]GS.

Metalloproteases differ widely in their sequence and are the most diverse of the mechanistic classes of proteases. More than 50 families of metalloprotease are classified to date but in all, a divalent cation (usually zinc) activates a water molecule which then attacks the carbonyl group of the scissile bond. The metal ion is bound by amino acids, typically three from the group of His, Glu, Asp or Lys. One further residue is required and at least one other residue is required for catalysis, which plays a role as a proton acceptor. An HEXXH motif that holds the divalent metal is found in about half the known metalloproteases. This motif may be more stringently defined as "abXHEbbHbc" where "a" is usually valine or threonine, "b" is an uncharged amino acid and "c" is a hydrophobic residue.

In some embodiments, the present invention provides polypeptides and polynucleotides encoding the polypeptides, wherein the polypeptides are characterized as a thermostable metallopeptidases which specifically cleave N-terminally to arginine and lysine. The thermostability of these peptidases provides substantial advantage over previously characterized proteases for two reasons. First, enzymes operate more rapidly at higher temperature. Thus, for a given ratio of protease to protein substrate (which will be hydrolyzed), a thermostable protease operating at a high temperature will require less time than a non-thermostable protease. Second, high temperatures denatures most proteins of mesophilic organisms, allowing proteolytic digestion of otherwise protease resistant molecules such as the prion protein of Mad Cow disease or amyloid fibrils in Alzheimer's disease.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions), and therein remain isolated polynucleotides or polypeptides within the meaning of that term as it is employed herein.

Plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

Nucleic acid sequences which encode a fusion protein can be operatively linked to expression control sequences. "Operatively linked" refers to a juxtaposition wherein the components so described are in a relationship permitting them to function in their intended manner. An expression control sequence operatively linked to a coding sequence can be ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., Methods in Enzymology 153:516-544, 1987). For example, when cloning in bacterial expression systems, inducible promoters such as pL of bacteriophage y, plac, ptrp, ptac (ptrp-lac hybrid promoter) and the like may be used. When cloning in mammalian cell expression systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In embodiments of the present invention, the nucleic acid sequences encoding a fusion protein of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Bioi. Chem. 263:3521, 1988), baculovirus derived vectors for expression in insect cells, cauliflower mosaic virus, CaMV; tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., Molecular Cloning-A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). These elements are well known to one of skill in the art.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516-544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedron gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a thermostable peptidase), or fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV 40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell, including a human cell.

Eukaryotic expression systems, and mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used. Such host cell lines may include but are not limited to CHO, VERO, BHK, HeLa, COS, MDCK, Jurkat, HEK-293, and W138.

Mammalian expression systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the thermostable peptidase in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Viral. 49:857-864, 1984; Panicali, et al., Proc. Natl. Acad. Sci. USA 79:4927-4931, 1982). of particular interest are vectors based on bovine papilloma virus which have the ability to replicate as extrachromosomal elements (Sarver, et al., Mol. Cell. Bioi. 1:486, 1981). Shortly after entry of this DNA into mouse cells, the plasmid replicates to about 100 to 200 copies per cell. Transcription of the inserted eDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the thermostable peptidase gene in host cells (Cone & Mulligan, Proc. Natl. Acad. Sci. USA, 81:6349-6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the eDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprC or a pre cells respectively. Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Bioi. 150:1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difiuoromethyl) DL-ornithine, DFMO (McConlogue L., In: Current Communications in Molecular Biology, Cold Spring Harbor Laboratory, ed., 1987).

In accordance with one embodiment of the present invention, there are provided isolated polypeptides characterized as thermostable metalloproteases with N-terminal specificity for arginine and lysine, or functional fragments thereof.

The present invention addresses this problem by disclosing enzymes with N-terminal Arg/Lys specificity in contrast to Lys only. It thus provides a method of determining a highly interpretable, unambiguous spectrum which can be interpreted without reference to databases. According to this invention, the method provides MS/MS spectra with ion current predominantly present in b-ions (in CID) or c-ions (in ETD) for the great majority of peptides. Moreover, the thermophilic metalloprotease identified, expressed and characterized herein and shown their behavior in mass spectrometry to accomplish this. Their thermophilic nature means that digestion times can be reduced vis-à-vis trypsin, also a desirable trait.

Methods and Modes for Carrying Out the Invention

Aspects of the present teachings can be further understood in light of the following examples, which should not be construed as limiting the scope of the present teachings in any way.

These enzymes are commercializable as such: researchers frequently buy proteases to analyze proteins. In the case of those we discovered, under the appropriate conditions they represent a potential direct substitution for trypsin. This protease has two minor disadvantages. First, all programs for searching mass spectrometric data now expect a mixture of ions from both the N- and C-termini; scores for peptides from our enzymes are thus typically lower. Second, as they are metalloproteases, they are not likely to work in the presence of EDTA or other chelators commonly used to prevent endogenous metalloprotease activity.

In our solution, we make the above enzymes either via in vitro transcription or by expression in *E. coli*. In the latter case, His$_6$-tagging and IMAC affinity was employed.

Enzyme thus purified was highly active and was stored with EDTA. Enzymes were activated in the presence of around 2.5 mM $CaCl_2$ and around 0.1 mM $ZnCl_2$ typically in buffers around 25-50 mM ammonium acetate or triethylammonium acetate, both of which are compatible with mass spectrometry. After digestion under these conditions with reasonable concentration of enzyme (from about 1:10 to 1:500 weight:weight of protein-substrate:protease) for some reasonable incubation period (from about 0.5 hr to 16 hr) at a temperature between around 20° C. to 100° C. (time, temperature and protease concentration depending on the particular digestion susceptibility of the substrate protein), specifically cleaved peptides suitable for mass spectrometric analysis, de novo sequencing and database searching by fragmentation techniques result.

The polypeptides of the present invention (e.g., a metallo-ArgLysN or ArgLysN) were purified in their inactive state by the immediate addition of ethylenediaminetetraacetic acid (EDTA) and dithiothreitol (DTT) after expression or synthesis in any manner. The activity was restored by the addition of divalent ions, in particular calcium around 1-5 mM and zinc around 0.1-0.5 mM. Phenymethylsulfonyl fluoride (PMSF) has no effect on the enzymatic activity of the polypeptide. The molecular mass of the described ArgLysN enzymes was monomeric as determined by intact mass ESI.

ArgLysN was able to efficiently digest proteins at enzyme: protein-substrate ratios from 1:20 to 1:500 at temperatures between room temperature and 100° C. for times between 0.5 hr and 18 hr. The exact length of time and enzyme required depend on the particular digestion susceptibility of the substrate protein. ArgLysN was active over a broad range of pH from 3-10. However, its specificity was lost when digestions were performed at pHes significantly different from neutral. Preferred digestion pH was in the range of 5-9. ArgLysN exhibited high specificity toward N-terminal cleavage of lysine and arginine residues. Consistently >80% of peptides were "fully ArgLysN specific" in that they began with an arginine or lysine and terminate at the reside before an arginine or lysine. E.g. KPEPTIDE[cut]R is a "fully ArgLysN specific" peptide. In the <20% of cases which are not "fully ArgLysN specific," like trypsin, ArgLysN is not an effective protease and will cut between two arginine or lysine residues but not cleave an extra from the end of a peptide. By example, treatment of the peptide TESTKPEPTIDERKAT with ArgLysN would likely produce the peptides TEST, KPEPDIEDR and KAT. Removal of the trailing R in KPEPDIEDR requires exopeptidase activity, of which ArgLysN possessed little.

The present invention further relates to thermostable peptidase enzymes that comprise the amino acid sequence as set forth in any of SEQ ID NOs: 1-4, as well as fragments, analogs and derivatives thereof.

The terms "fragment", "derivative", and "analog" when referring to the polypeptide and enzyme of the present invention means enzymes which retain essentially the same biological function or activity as such enzymes. Such biological activity includes, for example, the ability to hydrolyze peptide bonds and antigenicity. Thus, an analog includes a proprotein which can be activated by cleavage of the proprotein portion to produce an active mature enzyme.

The novel enzymes disclosed herein may be a recombinant enzyme or a synthetic enzyme, preferably a recombinant enzyme.

Example 1: Preparation of Recombinant Ch. Therm

Selection of Target Constructs

In order to screen for a construct with high specific activity that could also be produced recombinantly, synthetic genes corresponding to an array of metalloproteases with homology to LysN and ulilysin were ordered from GeneWiz. These putative targets were selected by phylogenetic alignment to known proteases and codon optimized for expression in *E. coli*. It should also be noted that as many endopeptidases are expressed as pro-proteins in nature, the pro-peptide was excluded from the construct design. Each synthetic gene also included PCR handles that could be used to amplify the target insert for direct assessment using in vitro transcription/translation methods (IVT; see Example 2 below). After assessment of the proteolytic activity of these constructs in the IVT assay, the top candidates were selected for cloning, recombinant expression, and purification.

Preparation of cDNA Constructs

Of the constructs screened, the putative MEP1-like metalloprotease from *Chaetomium thermophilum* (Ch. therm) was the most promising. The cDNA for this protein was cloned into the vector pRSF for expression in *E. coli*. Cloning was performed using standard sequence and ligation-independent cloning (SLIC) methods. The sequence fidelity of all constructs was verified by the Cold Spring Harbor Laboratory DNA Sequencing Facility. The final construct consisted of an N-terminal $His_6$-tag followed by a TEV cleavage site followed by the mature Ch. therm protein sequence.

Final cDNA and Protein Sequence for Ch. Therm

SEQ ID NO: 7
AT<u>G</u><u>CACCATCATCACCATCAC</u>*GGCGGC*<u>GAAAACCTGTATTTCCAG</u>

<u>*GGCGGA*</u>AAGCCGTTACCACCATCGATGCCTATTTTCATGTTGTTG

CAAAAAACACCAGCCTGAGCGGTGGTTATCTGACCGATGCAATGCTG

AATAATCAGCTGAATGTTCTGAATGCAGCATATGCACCGCATGGCTTT

CAGTTCAATCTGAAAGGTATTACCCGTACCGTTAATGCAAATTGGGCA

GATGATACCAAAGGCTATGAAATGACCATGAAACGTAGCCTGCGTAAA

GGCACCTATCGTACCCTGAATGTTTATTATCTGTATGAGATGGGTAGC

AACCTGGGCTATTGTTATTTTCCGCAGAGCGTTACCAGCGGTAGCACC

GCATTTTATCGTGATGGTTGTACCGTTCTGTATAGCACCGTTCCGGGT

GGTAGCCTGACCAATTATAACCTGGGTCATACCACCACCCATGAAGTT

GGTCATTGGATGGGTCTGTATCATACATTTCAGGGTGGTTGCACCGGT

AGCGGTGATTATGTTAGCGATACACCGGCACAGGCAAGCGCAAGCAGC

GGTTGTCCGATTGGTCGTGATAGCTGTCCGAGCCAGCCTGGTCTGGAT

CCGATTCATAATTACATGGATTATAGCTACGATAGCTGCTACGAAGAA

TTTACCGCAGGTCAGCAGGCACGTATGGTTAGCTATTGGAATAACTAT

CGTGCCGGTAAA<u>TAATAA</u>

SEQ ID NO: 8
M<u>HHHHHH</u>*GG*<u>ENLYFQ</u>*GG*KAVTTIDAYFHVVAKNTSLSGGYLTDAML

NNQLNVLNAAYAPHGFQFNLKGITRTVNANWADDTKGYEMTMKRSLRKG

TYRTLNVYYLYEMGSNLGYCYFPQSVTSGSTAFYRDGCTVLYSTVPGGS

-continued

LTNYNLGHTTTHEVGHWMGLYHTFQGGCTGSGDYVSDTPAQASASSGCP

IGRDSCPSQPGLDPIHNYMDYSYDSCYEEFTAGQQARMVSYWNNYRAG

K(-)(-)

Bold means —Initiator methionine
Bold Italic means—Glycine linkers
Underline means—His$_6$-tag
Italic and underline means—TEV site (cleavage occurs between Q and G)
Bold Underline means—(-) stop codon Recombinant Protein Expression Recombinant plasmids bearing cDNA for the target construct was transformed into *E. coli* BL21(DE3) RIPL by heat shock and grown on lysogeny broth (LB) agar plates containing the appropriate antibiotic. After overnight incubation at 37° C., single colonies were inoculated into a starter culture of LB media with antibiotic and grown at 37° C. with shaking at 220 rpm. After ~16 h, this starter culture was used to inoculate terrific broth (TB) media with antibiotic (50 mL of starter culture added per liter of TB) to an initial $OD_{600}$ of ~0.1. These cultures were then incubated at 37° C. with shaking at 300 rpm. The cell density was monitored and after ~4 hours ($OD_{600}$ of 1.0), the cultures were briefly cooled on ice, and protein expression was induced with 1 mM isopropyl-β-d-1-thiogalactopyranoside (IPTG). Cultures were then incubated at 16° C. with shaking at 300 rpm. After overnight induction, the cells were harvested at 4000 g for 20-30 minutes at 4° C. The resulting cell pellet was frozen and stored at –80° C. until needed.

Affinity Purification

After thawing the cell pellets, cells were resuspended in 20 mL of 50 mM sodium phosphate, pH 8.0, 50 mM NaCl, and 10 mM imidazole. The resuspended cells were then lysed by sonication (2 seconds on, 2 seconds off for a total sonication time of 2 minutes). Cell debris was then removed by centrifugation at 35000 g for 45 minutes. The resulting supernatant was purified by affinity chromatography on Ni-NTA resin (Qiagen). The target protein was eluted from the column with 50 mM sodium phosphate, pH 8.0, 0.2 M NaCl, 200 mM imidazole. EDTA was immediately added to the elution to prevent proteolysis at a final concentration of 10 mM.

Optional Removal of the Affinity Tag

For some preparations, the N-terminal affinity tag was removed by cleavage with TEV protease to produce SEQ ID NO: 2. To accomplish this, TEV protease (1:20 m/m ratio target/protease) was added to the elution. The reaction was incubated at 4° C. for ~16 hours. As the removal of the tag did not seem to affect the activity of Ch. therm, most preparations omitted this step.

Refolding and Buffer Exchange

To this point, the purified protein had no appreciable proteolytic activity when assayed using conditions similar to those used with the IVT-produced protein. Based on this observation, we proposed that that the reducing environment of the bacterial cytoplasm was interfering with proper folding and disulfide formation of the target construct. To restore activity to the misfolded protein, the purified material was unfolded with 6 M guanidine hydrochloride and reduced completely with 10 mM dithiothreitol. The protein was then slowly refolded by dialysis into 20 mM HEPES, pH 7.4, 100 mM NaCl, 2.5 mM cysteinine, 5 mM cysteamine, 2 mM EDTA, at 4° C. The dialysis procedure took place over ~16 hours with the buffer being exchanged once. After this initial dialysis step, the protein was further dialyzed into 20 mM HEPES, pH 7.4, 100 mM NaCl, 2 mM EDTA at 4° C. to remove the reductants.

Final Enzyme Preparation and Assessment

After dialysis, the protein solution was filtered using a 0.2 µm syringe, concentrated as desired using Amicon Ultra centrifugal filter devices, and stored at 4° C. The purity of each preparation was assessed by SDS-PAGE and the yield determined from absorbance at 280 nm and the calculated extinction coefficient. The intact mass of each preparation was also assessed electrospray ioniziation mass spectrometry (ESI-MS) and verified to within 1.0 Dalton.

Figure 3:
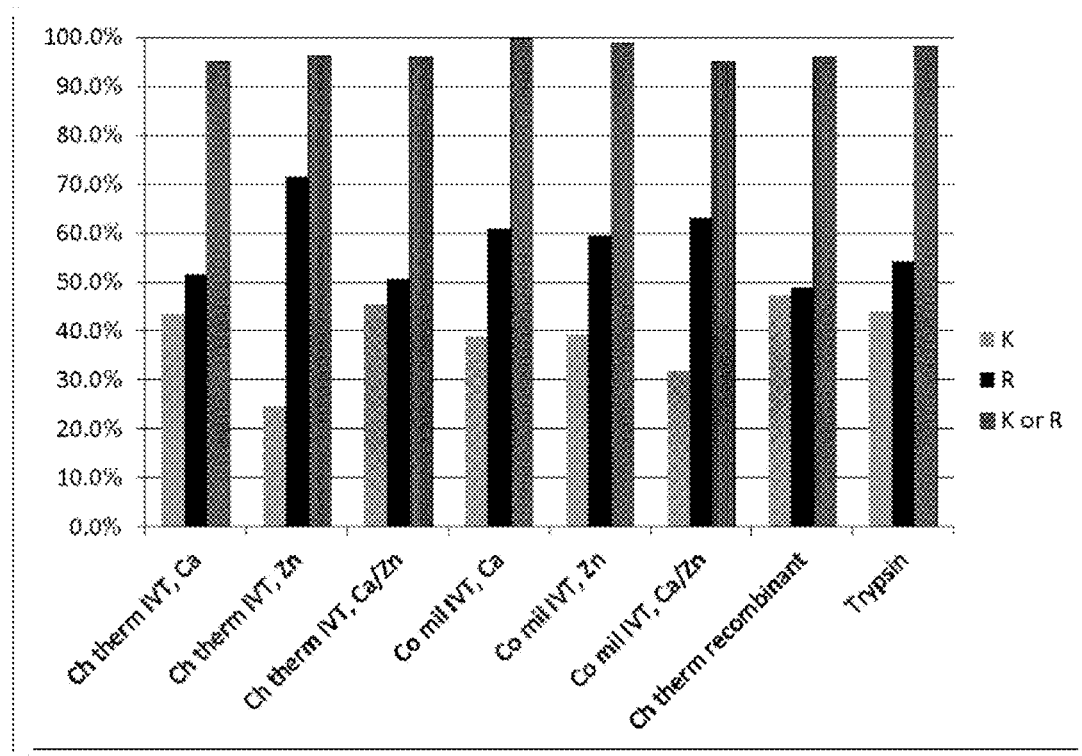
FIG. 3 illustrates enzyme specificity.
Figure 4:
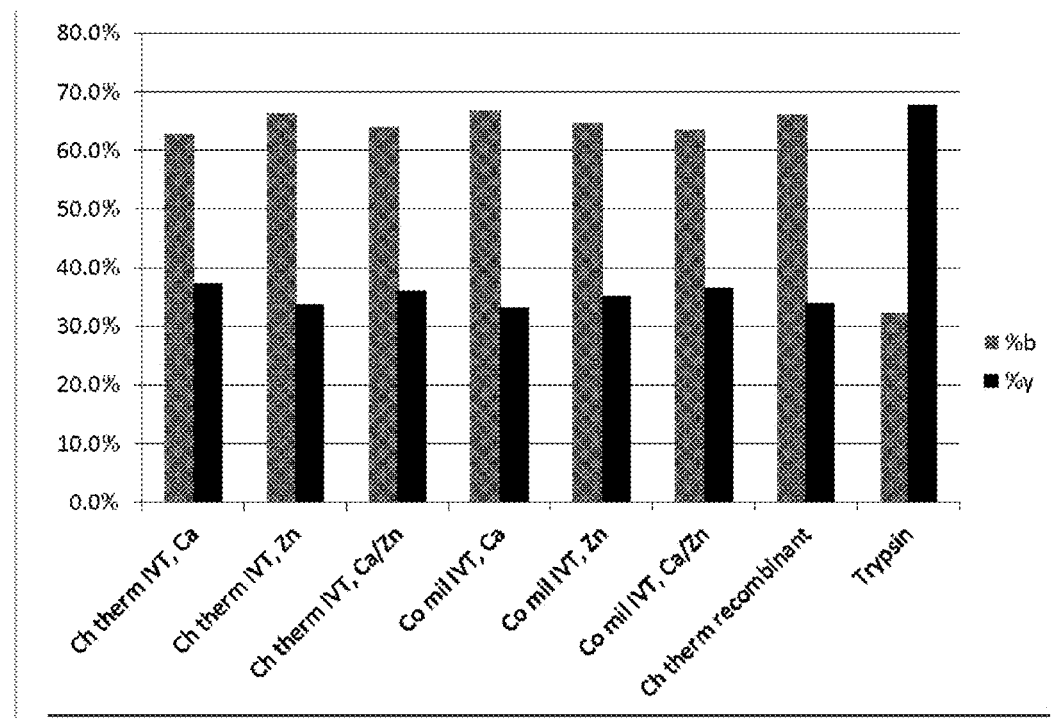
FIG. 4 illustrates the relative distribution of ion current between b- and y-ion series.

Analysis of Enzymatic Specificity 1 ug of enzyme prepared as above was added to 50 ug of *E. coli* lysate in 25 mM trimethylammonium acetate containing a final concentration of 0.1 mM $ZnCl_2$ and 2 mM $CaCl_2$. This mixture was incubated for 3 hrs at 55° C. 1 ug of this digest was subjected to LCMSMS on an Orbitrap XL. The resulting RAW file was searched with Mascot against the Uniprot database of *E. coli* using no enzyme specificity, 20 ppm precursor and 0.6 Da fragment tolerance. Specificity was calculated based on the "pep_res_after" column of a Mascot peptide export (the residue following the detected peptide). Ion current of the y- and b-series was calculated from the ion intensities of those ions reported in an mzIdentML export. Results obtained are listed in FIGS. 3 and 4. For comparison, results of the same analysis done of a standard trypsin digest (50 mM TEAB, 1:50 wt/wt, 37 C ON incubation) is included in the figure.

Example 2: Cell-Free Preparation of Recombinant Ch. Thermophilium and Co. *Militaris* Proteases New England Biolabs' PURExpress In Vitro Protein Synthesis kit (NEB #E6800) was used to make protein of SEQ ID NO: 3 and SEQ ID NO: 4 with no leader sequence. 10 uL of solution A (NEB kit), 7.5 uL of solution B (NEB kit), 0.5 uL of RNase inhibitor and 245 ng of template DNA encoding for SEQ ID NO: 3 and SEQ ID NO: 4 was combined with sufficient nuclease free water to bring the total reaction volume to 25 uL. This was mixed and incubated at 37° C. 2-4 hours without shaking. New protein bands were visible by gel, indicating the presence of new polypeptides. To this solution was added 75 uL of denaturation buffer (6 M guanidinium HCl, 50 mM tris pH 8.0, 2 mM EDTA, 10 mM DTT) and the resultant mixture was incubated for 10 min. at room temperature (RT). To this solution was then added 1 mL of renaturation buffer (1 mM Pefablock, 2.5 mM cystamine, 5 mM Cysteamine, 2.5 mM EDTA, 50 mM tris pH 7.4, 100 mM NaCl, 20% NDSB 201) and the resultant mix was incubated overnight at 4° C. After ON incubation, the solution was concentrated at 14,000 g with an Amicon 0.5 10 kDa spin filter. The retentate was washed three times with 200 uL of 25 mM ammonium acetate pH 7.4. The spin filter was inverted and spun 2 min at 1000 g into a new tube to collect the retentate (~30 uL).

Analysis of Enzymatic Specificity

Three 15 uL aliquots of this solution was brought to 100 uL 25 mM ammonium acetate pH 7.4 containing 1) 2 mM $CaCl_2$; 2) 0.1 mM $ZnCl_2$; and 3) 2 mM $CaCl_2$ plus 0.1 mM $ZnCl_2$ (three different digestion buffers). These were incubated ON at 37 C and the resultant solution was clarified by centrifugation. 2 uL of the resultant digests were subjected to LCMSMS on an Orbitrap XL. The resulting RAW file was searched with Mascot against the Uniprot database of *E. coli* using no enzyme specificity, 20 ppm precursor and 0.6 Da fragment tolerance. Specificity was calculated based on the "pep_res_after" column of a Mascot peptide export (the residue following the detected peptide). Ion current of the y- and b-series was calculated from the ion intensities of those ions reported in an mzIdentML export.

iTRAQ and TMT tags are plagued by interference of reporter ion signal from peptides which are close in mass, fall in the same selection mass window and are thus simultaneously fragmented. In these cases, the reporter ions are derived from both peptides, so the ratios are averaged. MS2/MS3 experiments offer a solution to this problem. In MS2, a selected ion (or mixture of ions) is fragmented by CID or other dissociation method, typically yielding backbone b- and y-ions. MS3 is subsequently performed by selecting and fragmenting one or more of the fragment ions. The reporter ions from this step can come only from that fragment, essentially removing background and giving a true reflection of relative reporter ion intensity. Selection of fragments for MS3 is often by intensity; it is thus unknown beforehand if a b- or y-ion was fragmented. In the case of tryptic peptides with arginine at the C-terminus, only b-ions give reporter ions. Y-ions, while giving no reporter signal, are abundant and intense. Thus, approximately half of tryptic peptides give limited or no reporter ions for quantitation. Using the ion current invention of this invention, the most intense ions selected for fragmentation will almost always be b-ions, thus always give reporter ions and significantly increasing the success rate in MS2/MS3 experiments compared to trypsin.

Sequence Listing

```
                                        SEQ ID NO: 1
Organism: Chaetomium thermophilum
MHHHHHHGGENLYFQGGKAVTTIDAYFHVVAKNTSLSGGYLTDAMLNNQLN

VLNAAYAPHGFQFNLKGITRTVNANWADDTKGYEMTMKRSLRKGTYRTLNV

YYLYEMGSNLGYCYFPQSVTSGSTAFYRDGCTVLYSTVPGGSLTNYNLGHT

TTHEVGHWMGLYHTFQGGCTGSGDYVSDTPAQASASSGCPIGRDSCPSQPG

LDPIHNYMDYSYDSCYEEFTAGQQARMVSYWNNYRAGK

SEQ ID NO: 2
Organism: Chaetomium thermophilum
GGKAVTTIDAYFHVVAKNTSLSGGYLTDAMLNNQLNVLNAAYAPHGFQFNL

KGITRTVNANWADDTKGYEMTMKRSLRKGTYRTLNVYYLYEMGSNLGYCYF

PQSVTSGSTAFYRDGCTVLYSTVPGGSLTNYNLGHTTTHEVGHWMGLYHTF

QGGCTGSGDYVSDTPAQASASSGCPIGRDSCPSQPGLDPIHNYMDYSYDSC

YEEFTAGQQARMVSYWNNYRAGK

SEQ ID NO: 3
Organism: Chaetomium thermophilum
KAVTTIDAYFHVVAKNTSLSGGYLTDAMLNNQLNVLNAAYAPHGFQFNLKG

ITRTVNANWADDTKGYEMTMKRSLRKGTYRTLNVYYLYEMGSNLGYCYFPQ
```

```
                                        -continued
SVTSGSTAFYRDGCTVLYSTVPGGSLTNYNLGHTTTHEVGHWMGLYHTFQG

GCTGSGDYVSDTPAQASASSGCPIGRDSCPSQPGLDPIHNYMDYSYDSCYE

EFTAGQQARMVSYWNNYRAGK

SEQ ID NO: 4
Organism: Cordyceps militaris
KLAEVNVPVYIHVVASSQSKADGYLSEADVRATVSGMNNDYQGLGFQFTVK

GVDHTINANWASDQDALGMKKKLRTGDYRTLNLYFLPKMAPNGRCYYPTTA

APGSTAFYNDGCTMRSDVYNNGQTTTHEVGHWLGLFHTFQDGCDPVNDMVS

DTPALINSWSCNTNDDSCPDMPGKDPVTNFMSYGTCRSVFTPGQTARMSSM

YNKYRA

SEQ ID NO: 5
MHHHHHH

SEQ ID NO: 6
MHHHHHHGGENLYFQGG
```

Example 3. Preparation of Support-Bound Enzyme

Solid-phase coupled protease can be prepared by example with cyanogen bromide activated Sepharose beads (CNBr-Sepharose). Lyophilized CNBr-activated Sepharose 4B is prepared by swelling and washing in 1 mM HCl for at least 15 min. Approximately 5 ml coupling buffer is used per gram of lyophilized powder, which will become about 3.5 ml final bed volume of beads. Enzyme is buffer exchanged or dissolved in coupling buffer, 0.1 M $NaHCO_3$, pH 8.3 containing, 0.5 M NaCl. About 5-10 mg of protease is added per mL of bed volume in a stoppered vessel which is rotated end-over-end for 1 h at room temperature or overnight at 4° C. Other gentle stirring methods may be employed but magnetic stirrers are to be avoided as these can disrupt the Sepharose beads. Excess ligand is washed away excess ligand with at least 5 bed volumes of coupling buffer and any remaining active groups are blocked by addition of 0.1 M Tris-HCl buffer, pH 8.0 or 1 M ethanolamine, pH 8.0, which is allowed to stand for 2 hours. The now solid phase supported protease is washed with at least 5 bed volumes and at least three cycles of alternating pH, low pH being a 0.1 M acetic acid/sodium acetate, pH 4.0 buffer containing 0.5 M NaCl followed by high pH washes of with 0.1 M Tris-HCl, pH 8 containing 0.5 M NaCl. The beads are then stored typically cold around neutral pH or might optionally be lyophilized for long-term storage. Many other solid phase supports and chemistries are known, commercially available and familiar to one skilled in the art.

While the present teachings are described in conjunction with various embodiments, it is not intended that the present teachings be limited to such embodiments. On the contrary, the present teachings encompass various alternatives, modifications and equivalents, as will be appreciated by those of skill in the art.

We claim:

1. An isolated polypeptide consisting of SEQ ID NO: 1, wherein the polypeptide has specific peptidase activity directed to the N-terminal side of lysine and arginine.

2. The isolated polypeptide of claim 1, wherein said polypeptide is created in an expression system.

3. The isolated polypeptide of claim 1, wherein said specific peptidase activity is thermostable.

4. A composition comprising a polypeptide of claim 1 covalently coupled to a solid support.

5. A kit comprising a polypeptide of claim 1, and optionally further comprising:
   a) a mass spectrometric digestion buffer around pH 3-10; and/or
   b) a stopping reagent.

6. A method of making the polypeptide of claim 1, wherein the method comprises:
   a) expressing the polypeptide from an expression system,
   b) optionally, inactivating said polypeptide to prevent autolysis,
   c) isolating said expressed polypeptide, and
   d) optionally reactivating said expressed polypeptide.

7. A method comprising:
   a) contacting the polypeptide of claim 1 with one or more proteins of interest to thus specifically produce fragment peptides with N-terminal arginine and N-terminal lysine residues;
   b) ionizing said fragment peptides to generate precursor ions;
   c) dissociating said ionized fragment peptides by CID, ETD, HCD or HTD or PSD to generate an N-terminal ladder of peptide fragment ions;
   d) measuring the intensity of said fragment ions as a function of mass to charge (m/z) ratio; and
   e) determining the protein sequence of one or more of the proteins of interest from the mass to charge ratios of the fragment ions.

* * * * *

SEQUENCE LISTING

<160> NUMBER OF SEQ ID NOS: 8

<210> SEQ ID NO 1
<211> LENGTH: 242
<212> TYPE: PRT
<213> ORGANISM: Chaetomium thermophilum

```
<400> SEQUENCE: 1

Met His His His His His Gly Gly Glu Asn Leu Tyr Phe Gln Gly
1               5                   10                  15

Gly Lys Ala Val Thr Thr Ile Asp Ala Tyr Phe His Val Val Ala Lys
            20                  25                  30

Asn Thr Ser Leu Ser Gly Gly Tyr Leu Thr Asp Ala Met Leu Asn Asn
                35                  40                  45

Gln Leu Asn Val Leu Asn Ala Ala Tyr Ala Pro His Gly Phe Gln Phe
    50                  55                  60

Asn Leu Lys Gly Ile Thr Arg Thr Val Asn Ala Asn Trp Ala Asp Asp
65                  70                  75                  80

Thr Lys Gly Tyr Glu Met Thr Met Lys Arg Ser Leu Arg Lys Gly Thr
                85                  90                  95

Tyr Arg Thr Leu Asn Val Tyr Leu Tyr Glu Met Gly Ser Asn Leu
                100                 105                 110

Gly Tyr Cys Tyr Phe Pro Gln Ser Val Thr Ser Gly Ser Thr Ala Phe
            115                 120                 125

Tyr Arg Asp Gly Cys Thr Val Leu Tyr Ser Thr Val Pro Gly Gly Ser
    130                 135                 140

Leu Thr Asn Tyr Asn Leu Gly His Thr Thr Thr His Glu Val Gly His
145                 150                 155                 160

Trp Met Gly Leu Tyr His Thr Phe Gln Gly Gly Cys Thr Gly Ser Gly
                165                 170                 175

Asp Tyr Val Ser Asp Thr Pro Ala Gln Ala Ser Ala Ser Ser Gly Cys
            180                 185                 190

Pro Ile Gly Arg Asp Ser Cys Pro Ser Gln Pro Gly Leu Asp Pro Ile
    195                 200                 205

His Asn Tyr Met Asp Tyr Ser Tyr Asp Ser Cys Tyr Glu Glu Phe Thr
    210                 215                 220

Ala Gly Gln Gln Ala Arg Met Val Ser Tyr Trp Asn Asn Tyr Arg Ala
225                 230                 235                 240

Gly Lys

<210> SEQ ID NO 2
<211> LENGTH: 227
<212> TYPE: PRT
<213> ORGANISM: Chaetomium thermophilum

<400> SEQUENCE: 2

Gly Gly Lys Ala Val Thr Thr Ile Asp Ala Tyr Phe His Val Val Ala
1               5                   10                  15

Lys Asn Thr Ser Leu Ser Gly Gly Tyr Leu Thr Asp Ala Met Leu Asn
                20                  25                  30

Asn Gln Leu Asn Val Leu Asn Ala Ala Tyr Ala Pro His Gly Phe Gln
            35                  40                  45

Phe Asn Leu Lys Gly Ile Thr Arg Thr Val Asn Ala Asn Trp Ala Asp
    50                  55                  60

Asp Thr Lys Gly Tyr Glu Met Thr Met Lys Arg Ser Leu Arg Lys Gly
65                  70                  75                  80

Thr Tyr Arg Thr Leu Asn Val Tyr Leu Tyr Glu Met Gly Ser Asn
                85                  90                  95

Leu Gly Tyr Cys Tyr Phe Pro Gln Ser Val Thr Ser Gly Ser Thr Ala
            100                 105                 110

Phe Tyr Arg Asp Gly Cys Thr Val Leu Tyr Ser Thr Val Pro Gly Gly
```

```
                115                 120                 125
Ser Leu Thr Asn Tyr Asn Leu Gly His Thr Thr His Glu Val Gly
    130                 135                 140

His Trp Met Gly Leu Tyr His Thr Phe Gln Gly Gly Cys Thr Gly Ser
145                 150                 155                 160

Gly Asp Tyr Val Ser Asp Thr Pro Ala Gln Ala Ser Ala Ser Ser Gly
                165                 170                 175

Cys Pro Ile Gly Arg Asp Ser Cys Pro Ser Gln Pro Gly Leu Asp Pro
                180                 185                 190

Ile His Asn Tyr Met Asp Tyr Ser Tyr Asp Ser Cys Tyr Glu Glu Phe
                195                 200                 205

Thr Ala Gly Gln Gln Ala Arg Met Val Ser Tyr Trp Asn Asn Tyr Arg
    210                 215                 220

Ala Gly Lys
225

<210> SEQ ID NO 3
<211> LENGTH: 225
<212> TYPE: PRT
<213> ORGANISM: Chaetomium thermophilum

<400> SEQUENCE: 3

Lys Ala Val Thr Thr Ile Asp Ala Tyr Phe His Val Val Ala Lys Asn
1               5                   10                  15

Thr Ser Leu Ser Gly Gly Tyr Leu Thr Asp Ala Met Leu Asn Asn Gln
                20                  25                  30

Leu Asn Val Leu Asn Ala Ala Tyr Ala Pro His Gly Phe Gln Phe Asn
            35                  40                  45

Leu Lys Gly Ile Thr Arg Thr Val Asn Ala Asn Trp Ala Asp Asp Thr
    50                  55                  60

Lys Gly Tyr Glu Met Thr Met Lys Arg Ser Leu Arg Lys Gly Thr Tyr
65                  70                  75                  80

Arg Thr Leu Asn Val Tyr Tyr Leu Tyr Glu Met Gly Ser Asn Leu Gly
                85                  90                  95

Tyr Cys Tyr Phe Pro Gln Ser Val Thr Ser Gly Ser Thr Ala Phe Tyr
            100                 105                 110

Arg Asp Gly Cys Thr Val Leu Tyr Ser Thr Val Pro Gly Gly Ser Leu
        115                 120                 125

Thr Asn Tyr Asn Leu Gly His Thr Thr His Glu Val Gly His Trp
    130                 135                 140

Met Gly Leu Tyr His Thr Phe Gln Gly Gly Cys Thr Gly Ser Gly Asp
145                 150                 155                 160

Tyr Val Ser Asp Thr Pro Ala Gln Ala Ser Ala Ser Ser Gly Cys Pro
                165                 170                 175

Ile Gly Arg Asp Ser Cys Pro Ser Gln Pro Gly Leu Asp Pro Ile His
            180                 185                 190

Asn Tyr Met Asp Tyr Ser Tyr Asp Ser Cys Tyr Glu Glu Phe Thr Ala
        195                 200                 205

Gly Gln Gln Ala Arg Met Val Ser Tyr Trp Asn Asn Tyr Arg Ala Gly
    210                 215                 220

Lys
225

<210> SEQ ID NO 4
<211> LENGTH: 210
```

<212> TYPE: PRT
<213> ORGANISM: Cordyceps militaris

<400> SEQUENCE: 4

```
Lys Leu Ala Glu Val Asn Val Pro Val Tyr Ile His Val Val Ala Ser
1               5                   10                  15

Ser Gln Ser Lys Ala Asp Gly Tyr Leu Ser Glu Ala Asp Val Arg Ala
            20                  25                  30

Thr Val Ser Gly Met Asn Asn Asp Tyr Gln Gly Leu Gly Phe Gln Phe
        35                  40                  45

Thr Val Lys Gly Val Asp His Thr Ile Asn Ala Asn Trp Ala Ser Asp
    50                  55                  60

Gln Asp Ala Leu Gly Met Lys Lys Leu Arg Thr Gly Asp Tyr Arg
65                  70                  75                  80

Thr Leu Asn Leu Tyr Phe Leu Pro Lys Met Ala Pro Asn Gly Arg Cys
                85                  90                  95

Tyr Tyr Pro Thr Thr Ala Ala Pro Gly Ser Thr Ala Phe Tyr Asn Asp
            100                 105                 110

Gly Cys Thr Met Arg Ser Asp Val Tyr Asn Asn Gly Gln Thr Thr Thr
        115                 120                 125

His Glu Val Gly His Trp Leu Gly Leu Phe His Thr Phe Gln Asp Gly
    130                 135                 140

Cys Asp Pro Val Asn Asp Met Val Ser Asp Thr Pro Ala Leu Ile Asn
145                 150                 155                 160

Ser Trp Ser Cys Asn Thr Asn Asp Asp Ser Cys Pro Asp Met Pro Gly
                165                 170                 175

Lys Asp Pro Val Thr Asn Phe Met Ser Tyr Gly Thr Cys Arg Ser Val
            180                 185                 190

Phe Thr Pro Gly Gln Thr Ala Arg Met Ser Ser Met Tyr Asn Lys Tyr
        195                 200                 205

Arg Ala
    210
```

<210> SEQ ID NO 5
<211> LENGTH: 7
<212> TYPE: PRT
<213> ORGANISM: Artificial Sequence
<220> FEATURE:
<223> OTHER INFORMATION: Purification handle

<400> SEQUENCE: 5

```
Met His His His His His His
1               5
```

<210> SEQ ID NO 6
<211> LENGTH: 17
<212> TYPE: PRT
<213> ORGANISM: Artificial Sequence
<220> FEATURE:
<223> OTHER INFORMATION: Purification Handle

<400> SEQUENCE: 6

```
Met His His His His His His Gly Gly Glu Asn Leu Tyr Phe Gln Gly
1               5                   10                  15

Gly
```

<210> SEQ ID NO 7
<211> LENGTH: 732
<212> TYPE: DNA

-continued

<213> ORGANISM: Chaetomium thermophilum

<400> SEQUENCE: 7

```
atgcaccatc atcaccatca cggcggcgaa aacctgtatt tccagggcgg aaaagccgtt    60
accaccatcg atgcctattt tcatgttgtt gcaaaaaaca ccagcctgag cggtggttat   120
ctgaccgatg caatgctgaa taatcagctg aatgttctga atgcagcata tgcaccgcat   180
ggctttcagt tcaatctgaa aggtattacc cgtaccgtta atgcaaattg gcagatgat   240
accaaaggct atgaaatgac catgaaacgt agcctgcgta aaggcaccta tcgtaccctg   300
aatgtttatt atctgtatga gatgggtagc aacctgggct attgttattt tccgcagagc   360
gttaccagcg gtagcaccgc attttatcgt gatggttgta ccgttctgta tagcaccgtt   420
ccgggtggta gcctgaccaa ttataacctg ggtcatacca ccacccatga agttggtcat   480
tggatgggtc tgtatcatac atttcagggt ggttgcaccg gtagcggtga ttatgttagc   540
gataccaccgg cacaggcaag cgcaagcagc ggttgtccga ttggtcgtga tagctgtccg   600
agccagcctg gtctggatcc gattcataat tacatggatt atagctacga tagctgctac   660
gaagaattta ccgcaggtca gcaggcacgt atggttagct attggaataa ctatcgtgcc   720
ggtaaataat aa                                                       732
```

<210> SEQ ID NO 8
<211> LENGTH: 242
<212> TYPE: PRT
<213> ORGANISM: Artificial Sequence
<220> FEATURE:
<223> OTHER INFORMATION: Engineered sequence with purification handle added

<400> SEQUENCE: 8

```
Met His His His His His Gly Gly Glu Asn Leu Tyr Phe Gln Gly
  1               5                  10                  15

Gly Lys Ala Val Thr Thr Ile Asp Ala Tyr Phe His Val Val Ala Lys
             20                  25                  30

Asn Thr Ser Leu Ser Gly Gly Tyr Leu Thr Asp Ala Met Leu Asn Asn
         35                  40                  45

Gln Leu Asn Val Leu Asn Ala Ala Tyr Ala Pro His Gly Phe Gln Phe
     50                  55                  60

Asn Leu Lys Gly Ile Thr Arg Thr Val Asn Ala Asn Trp Ala Asp Asp
 65                  70                  75                  80

Thr Lys Gly Tyr Glu Met Thr Met Lys Arg Ser Leu Arg Lys Gly Thr
                 85                  90                  95

Tyr Arg Thr Leu Asn Val Tyr Tyr Leu Tyr Glu Met Gly Ser Asn Leu
            100                 105                 110

Gly Tyr Cys Tyr Phe Pro Gln Ser Val Thr Ser Gly Ser Thr Ala Phe
        115                 120                 125

Tyr Arg Asp Gly Cys Thr Val Leu Tyr Ser Thr Val Pro Gly Gly Ser
    130                 135                 140

Leu Thr Asn Tyr Asn Leu Gly His Thr Thr Thr His Glu Val Gly His
145                 150                 155                 160

Trp Met Gly Leu Tyr His Thr Phe Gln Gly Gly Cys Thr Gly Ser Gly
                165                 170                 175

Asp Tyr Val Ser Asp Thr Pro Ala Gln Ala Ser Ala Ser Ser Gly Cys
            180                 185                 190

Pro Ile Gly Arg Asp Ser Cys Pro Ser Gln Pro Gly Leu Asp Pro Ile
        195                 200                 205
```

```
His Asn Tyr Met Asp Tyr Ser Tyr Asp Ser Cys Tyr Glu Glu Phe Thr
    210             215             220
Ala Gly Gln Gln Ala Arg Met Val Ser Tyr Trp Asn Asn Tyr Arg Ala
225             230             235             240
Gly Lys
```